United States Patent
Hinton et al.

[11] Patent Number: 5,485,502
[45] Date of Patent: Jan. 16, 1996

[54] RADIOGRAPHIC GANTRY WITH SOFTWARE COLLISION AVOIDANCE

[75] Inventors: Corydon A. Hinton, Monona; Glenn Szejna, Madison, both of Wis.

[73] Assignee: Lunar Corporation, Madison, Wis.

[21] Appl. No.: 280,632

[22] Filed: Jul. 26, 1994

[51] Int. Cl.⁶ .................................................. H05G 1/30
[52] U.S. Cl. ........................................ 378/117; 250/363.01
[58] Field of Search ................... 250/363.01, 363.04; 378/95, 117, 196, 197, 198, 204, 205, 208, 209

[56] References Cited

U.S. PATENT DOCUMENTS

| | | | |
|---|---|---|---|
| 3,822,875 | 7/1974 | Schmedemann | 5/601 |
| 3,891,856 | 6/1975 | Amor, Jr. et al. | 250/523 |
| 4,363,128 | 12/1982 | Grady et al. | 378/181 |
| 4,597,094 | 6/1986 | Kleinman | 378/95 |
| 4,922,430 | 5/1990 | Wavish | 364/461 |
| 4,969,170 | 11/1990 | Kilkuchi et al. | 378/91 |
| 4,987,583 | 1/1991 | Travanty et al. | 378/91 |
| 5,056,365 | 10/1991 | Gray et al. | 73/432.1 |
| 5,058,024 | 10/1991 | Inselberg | 364/461 |
| 5,150,026 | 9/1992 | Seraji et al. | 318/568 |
| 5,173,861 | 12/1992 | Inselberg et al. | 364/461 |
| 5,178,136 | 1/1993 | Wess et al. | 128/24 |
| 5,319,205 | 6/1994 | Kline et al. | 250/363.04 |

Primary Examiner—David P. Porta
Assistant Examiner—David Vernon Bruce
Attorney, Agent, or Firm—Quarles & Brady

[57] ABSTRACT

Computer control of a multi-axis radiographic instrument is utilized to prevent contact between moving surfaces of the instrument based on soft limits. The soft limits are established from a legal state table incorporating all combinations of axis movement of the equipment and relating those combinations to contacting or non-contacting states. The legal state table may be used to map efficient paths between a start and ending position and may be augmented with non-contacting transducers which may sense patient movement not incorporated into the legal state table.

10 Claims, 5 Drawing Sheets

RADIOGRAPHIC GANTRY WITH SOFTWARE COLLISION AVOIDANCE

FIELD OF THE INVENTION

The invention relates to radiographic equipment and specifically to a means for preventing collisions between components of such radiographic equipment, for example, a patient table and x-ray source.

BACKGROUND OF THE INVENTION

General purpose x-ray equipment typically has one or more movable arms upon which an x-ray source and x-ray detector may be mounted. The movable arms are designed to provide flexibility in positioning an x-ray beam passing between the x-ray source and detector, to a particular location in the patient and at a specific angle to the patient. The location and angle may be important in maximizing the diagnostic information contained in the image to be obtained.

Frequently, a series of different images of different regions and at different angles will be desired as part of a single routine or procedure. For example, with dual energy x-ray equipment used for measuring bone density, a common procedure may require the measurement of the density of the bones of the spine and hip at two different angles.

In some x-ray systems, positioning of the arms is done manually with the operator grasping handles near the radiation source, for example, to move the arm to its new position. The arm is typically counterbalanced, both so as to be easily movable and so as to remain at the new position without external support.

In more complex x-ray equipment, or x-ray equipment with larger radiation sources and detectors, the movement of the arms is done by motors that may be controlled either by a handheld pendant, held by the operator, or by instructions generated under computer control. The use of motors to move the arm permits the use of more sophisticated x-ray machine architectures, for example, architectures employing C-arms which improve patient access, but which are intrinsically unbalanced. The use of motors to control the motion of the arm also permits more accurate positioning of the arm, and is necessary for scanning systems where the source and detector must be precisely translated during the exposure.

When a motorized x-ray system is repositioned under operator control, the operator must observe all moving portions of the radiographic equipment to insure that there are no collisions between stationary and moving portions of the equipment. Likewise, the operator must ensure that no portion of the equipment strikes the patient. This is not always easy because the source and detector may be moving in opposite directions at spatially distant points.

This problem of properly monitoring the motion of the x-ray machine becomes increasingly difficult as the number of axes of motion permitted by the equipment increases. For this reason, pressure sensitive switches are typically placed at likely points of contact between components of the radiographic system. Such switches may have conductor pairs held in spaced opposition by an elastomer so as to contact each other only when the elastomer is deformed in a collision. An alternative switch is a sealed tube holding air whose pressure is monitored to detect deformation of the tube as might be caused by a collision.

When the radiographic system permits the movement of multiple axes, the best manner of moving the arm between two points is not always apparent and the operator's control of the arm to realize that motion may be slow and inefficient. This is particularly true where a given position may be apparently reached with more than one set of axes motions but where motion limits on one or more axes produces a "dead end" requiring a time consuming backtracking in order to reach the desired position.

SUMMARY OF THE INVENTION

The present invention provides an apparatus and method for controlling the motion of a radiographic system so as to follow an efficient path between two positions and to avoid collision between the various elements of that system.

Specifically, the radiographic system of the present invention includes a radiation source and a detector at least one of which may be held on an arm movable within movement limits to arm positions in at least two dimensions. The movement may be with respect to a patient support.

When such a system has an operator input device for providing command signals to initiate movement of the arm from a current arm position along a movement dimension, the system may further include an electronic computer communicating with the arm so as to determine the arm position and to provide motion signals for moving the arm between arm positions. The electronic computer may have a memory storing a legal space table that relates arm positions within the movement limits of the arm to contacting or non-contacting states. The memory may also have a program for controlling the electronic computer so as to receive command signals from the operator input device, indicating a desired movement dimension, and to search the legal space table from the current arm position through arm positions along the movement dimension until a first arm position related to a contact state is found. This first arm position is designated a soft limit. The program provides movement signals to the arm to move the arm in the movement direction only so long as the current arm position is before the soft limit.

Thus, it is one object of the invention to provide a sophisticated collision avoidance system that permits operator control of the arm movement but that can eliminate certain types of collisions prior to actual contact between the fixed and moving parts. The legal state table permits the ready evaluation of the free movement of the radiographic device in any dimension chosen by the operator.

It is another object of the invention to provide a collision avoidance system that is computationally efficient. The legal state table may be rapidly reviewed in real-time to determine whether a collision is likely. No complex mathematical analysis is required as might be necessary in other forms of modeling.

In an alternative embodiment, the movement instructions may be indicated as a single point in space rather than as a series of positioning commands input by an operator. When such a system is provided with a destination position, the program for controlling the computer determines a legal path along arm positions of the legal space table from the current arm position to the destination arm position. A legal path is one that does not cross any arm positions related to a contacting state.

This legal path may be found by searching the legal space table for an edge path along edges of an n-dimensional cube in the legal space table having opposed vertices equal to the current arm position and the destination arm position where n is the number of dimensions of the legal space table.

Thus, it is an object of the invention to automatically find a simple legal path between two points and requiring movement of only a single axis at a time.

Alternatively, an edge path may be sought and if an edge path is not found, the legal space table may be searched from the first arm position through arm positions along movement dimensions until an arm position related to a contact state is found, this arm position being designated a compass point limit. Each compass point limit may be examined to see if an edge path exists between the compass point limit and the destination. If so, the path is completed, if not, these steps are repeated.

Thus, is another object of the invention to automatically find a legal path between two points where a direct path along the edges of a cube having opposed corners being the start and destination point cannot be found.

The number of repetitions of the steps of this path finding process may be limited to a fixed number or may be successively increased until a path is found.

Thus, it is another object of the invention to provide a simple method of finding an optimal legal path joining two points without crossing a contacting state.

The program may repeat the steps of finding legal paths for a set of different predetermined arm positions.

Thus, it is another object of the invention to provide the ability to automatically position a radiographic system at a set of different sites separated in space without collision.

The foregoing and other objects and advantages of the invention will appear from the following description. In the description, reference is made to the accompanying drawings which form a part hereof and in which there is shown by way of illustration, a preferred embodiment of the invention. Such embodiment does not necessarily represent the full scope of the invention, however, and reference must be made therefore to the claims herein for interpreting the scope of the invention.

DETAILED DESCRIPTION OF THE PREFERRED EMBODIMENT

Radiographic System

Figure 1:
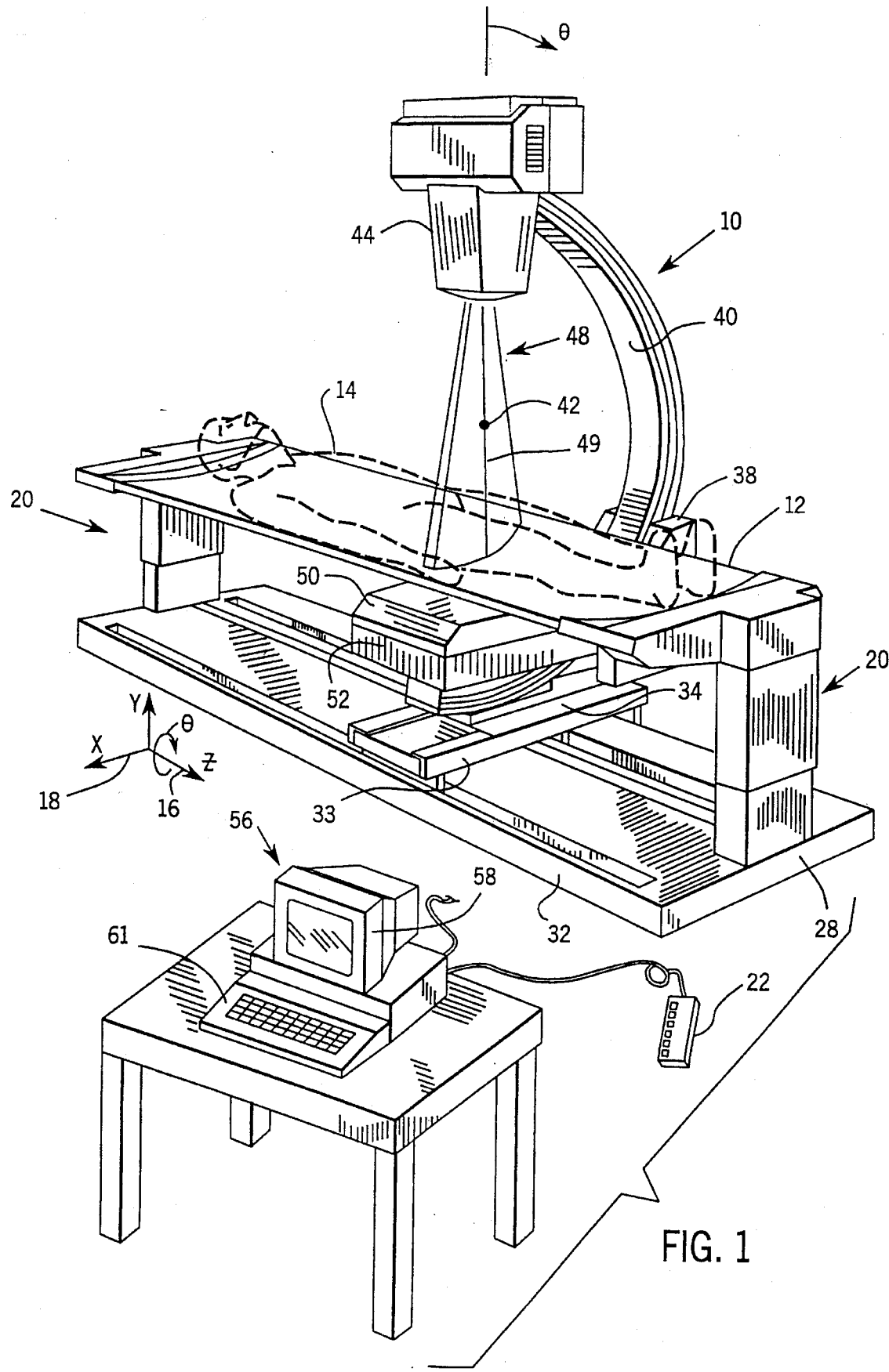
FIG. 1 is a perspective view of a scanning radiographic system per the present invention showing a C-arm holding an x-ray source and a detector, a table positioned for holding a patient, and a controlling computer for receiving data from the detector and moving the x-ray source and detector with respect to the table.

Referring to FIG. 1, a scanning radiographic system 10 constructed according to the present invention includes a table 12, for supporting a patient 14 before or after an examination (as shown), or during an examination, with the patient 14 in a supine position along a longitudinal or z-axis 16 of a Cartesian coordinate system.

Support pillars 20 hold the longitudinal ends of the table 12 and are attached at their bottom ends to a bed 28 supporting the radiographic system 10. The support pillars may telescope to move the table 12 up and down in the y-axis of the Cartesian coordinate system.

The bed 28 includes two longitudinal rails 32 which form a track for supporting a transversely extending gantry pallet 34, and which allow the gantry pallet 34 to be positioned longitudinally along substantially the entire length of the radiographic system 10 along the z-axis 16.

The gantry pallet 34 includes transverse rails 33 carried by rollers (not visible) fitting within the rails 32. Riding on the rails 33 of the gantry pallet 34 is a C-arm collar 38 which may be moved in the x-axis of the Cartesian coordinate system.

Collar 38 is generally arcuate to enclose and slideably hold a C-arm 40 such that the ends of the C-arm may rotate about a center 42 as the body of the C-arm 40 slides through the collar 38. Motion of the C-arm 40 moves the radiation source 44 and detector array 50 about a center 42 by an angle θ.

A radiation source 44, which is an x-ray tube, is mounted at one end of the C-arm 40 and is oriented to direct a polychromatic x-ray fan beam 48 along beam axis 49 generally towards the center 42 near the table 12. The table 12 is constructed of a radiolucent material to permit the free passage of x-rays of fan beam 48. The fan beam 48 emanates from a focal spot (not shown) within the x-ray tube and diverges to the sides of the beam axis 49 within the fan beam plane to define a fan beam angle $\phi$.

The fan beam 48 is received by a bi-linear detector array 50 mounted on the other end of the C-arm 40 and extending perpendicularly to the fan beam axis 49, within the fan beam plane, and generally on the opposite side of the patient 14 during examination. The detector array 50 is affixed to a stop plate 52 including a backing lead shield to prevent further transmission of the x-rays of the fan beam 48. The detector array 50, produces a set of electrical intensity signals indicating the intensity of the received x-rays of the fan beam 48.

Contact switches (not shown) are placed along the inner face of the detector 50, the radiation source 44 and the C-arm 40 to produce a contact signal indicating contact between these surfaces and another surface. These contact signals and the detector signals are communicated to a computer 56 in digitized form.

The computer 56, of a type such as is well known in the art, includes a keyboard 61 and display terminal 58, the latter for display of images formed of the signals from the detector array 50. The keyboard 61 permits the entry of operator commands to the control program. A hand-held pendant 22 attaches to the motion control card in computer 56 to provide command signals from an operator, by the pressing of buttons on the pendant, for moving the radiographic system 10 in each of its axes under operator control. The computer 56 also includes specialized motion control circuitry (in the form of a plug-in card), such as is commercially available, to permit the computer 56 to control the motion of a set of stepper motors (not shown) moving the different axes of the system 10.

The computer 56 executes a stored program that may thus provide control of the C-arm 40 in its motion through collar 38 and along the longitudinal and transverse axes 16 and 18 by means of the stepper motors (not shown). The motion of the C-arm 40 through collar 38 and along the longitudinal and transverse axes 16 and 18 is limited first by a software limit incorporated into the program, second by limit switches which stop the stepper motors when the limit switches are activated, and finally by hard stops which physically prevent more motion.

The program also controls the receipt of data from the detector array 50, the processing of that data and the turning on and off of the x-ray source 44 as may be required.

A radiographic system suitable for use with the present invention is described in further detail in U.S. application Ser. No. 07/976,797 entitled: *Patient Positioning Apparatus for Bone Scanning*, assigned to the assignee of the present application and hereby incorporated by reference.

Figure 2:
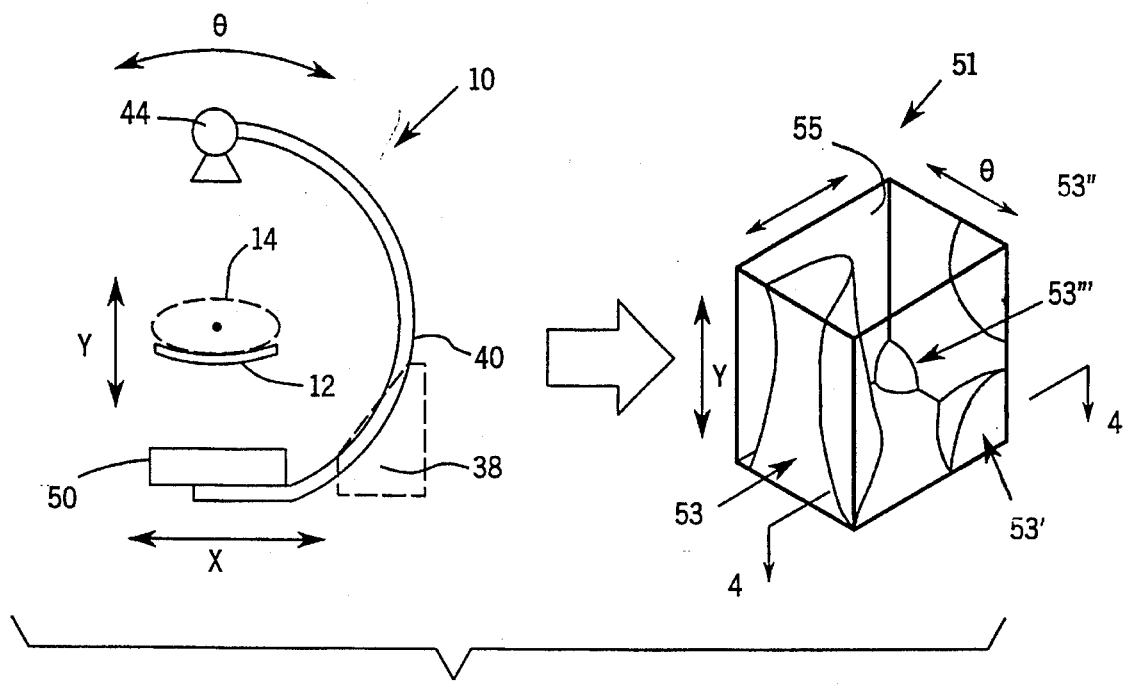
FIG. 2 is a simplified elevational view of the scanning radiographic system of FIG. 1 showing three of its axes of motion as translated to a legal space table having corresponding dimensions and identifying contacting and non-contacting areas.

Referring now to FIGS. 1 and 2, the radiographic system 10 provides relative motion between the x-ray source 44 and the x-ray detector 50 and the patient 14 in four dimensions: one corresponding to each of the three Cartesian coordinates of x, y and z and one corresponding to the angle $\theta$. Specifically, table 12 may be moved up and down in the y-axis. The C-arm may be moved transversely in the x-axis and longitudinally in the z-axis, and the C-arm 40 may be rotated in the $\theta$ axis.

For the purposes of identifying possible collisions between the radiation source 44, C-arm 40 and detector 50 and the table 12, the z-axis can be practically disregarded, that is, changes along the z-axis alone will not cause or avoid a collision between these components. Thus, in the present invention, only three dimensions need be considered: x, y and $\theta$.

Legal Space Table

The three remaining dimensions may be represented by a legal space table 51 (pictured in FIG. 2 as a rectangular prism) each dimension of which corresponds to a different one of the dimensions x, y and $\theta$. The boundaries of the legal space table 51 are determined by the physical limits imposed on each axis of the radiographic system 10. For example, the C-arm may move by 150 degrees before it hit stops at either end, thus, the dimensions of the legal space table 51 in $\theta$ is from $-100$ to $+50$ degrees. The two directions along each dimension may be arbitrarily designated by a positive and negative sign.

Each point within the cube of the legal space table 51 has a unique x, y and $\theta$ coordinate corresponding to a particular configuration of the C-arm 40 with respect to the table 12 as defined by those coordinates x, y and $\theta$.

The points of the legal space table 51 may be collected into contacting regions 53 and non-contacting regions 55. The contacting regions 53 include points whose coordinates x, y and $\theta$ correspond to C-arm 40 and table 12 positions which would result in contact between any one of the radiation source 44, C-arm 40 and detector 50 and the table 12. Preferably the table 51 is considered to include a protective envelope encircling a standard patient volume so that points in volume 53 indicate not merely contact between the C-arm 40, the radiation source 44 and the detector 50, and the table 12 but also contact with a volume that a patient might be expected to occupy.

The non-contacting regions 55 are the remaining volume of the legal space table 51 corresponding to coordinates y, x and $\theta$ where there is no contact between any one of the radiation source 44, C-arm 40 and detector 50 and the table 12. While generally contacting and non-contacting regions 53 and 55 within the legal space table 51 will be clustered into discrete volumes, there is no requirement that the regions of contacting points be contiguous.

By means of the legal space table 51, any position of the radiographic system 10 may be identified to either a contacting or non-contacting state. In practice, the legal space table 51 comprises a matrix of discrete "points" stored in memory locations within the computer 56 whose addresses may be related to unique combinations of the coordinates x, y and $\theta$ and whose contents indicate either a contacting or non-contacting state. The difference between consecutive values of the coordinates x, y and $\theta$ associated with the stored points is selected to be sufficiently small so a particular path of motion by the radiographic system 10 may be accurately approximated as a series of points in the legal space table 51, that is, if each of the points along the path is non-contacting, the path may be presumed to be non-contacting.

The data of the legal space table may be generated by modeling the radiographic system 10 on a computer according to methods well known in the art. The model may then be positioned in a series of discrete positions embracing all possible combinations of the x, y and $\theta$ coordinates. At each position, the model is tested to see if there is an overlap between any of its elements, e.g. the radiation source 44 and the table 12, such as would indicate contact. For example, for a given position of the table 12 (y-axis) and x-axis location of the C-arm 40, each angle of the C-arm might be evaluated for every degree within the range of the C-arm 40. Then, patient table 12 would then be moved in the y-axis by a millimeter and the process repeated. After the table 12 has moved by its full y-axis range, for every angle $\theta$, the C-arm is moved by one millimeter in the x direction and the entire process repeated until all possible x, y and $\theta$ positions have been analyzed. Of course it will be recognized, that the legal space table 51 may be implemented as the above computer model and the determination of contacting and non-contacting states computed as required. This however produces a significant increase in computational overhead.

A legal space table 51 is not limited to three dimensions but may be constructed for any radiographic system 10 whose positions may be uniquely identified by a finite set of coordinates. By adopting a general interpretation of the term "cube" to embrace the equivalents of a three dimensional cube in arbitrary n-dimensions, it will be apparent that a legal space table 51 will generally be an n-dimensional cube where n corresponds to the number of coordinates needed to uniquely describe the position of the radiographic system 10. For a radiographic system having four or more dimensions, the legal space table becomes a four dimensional cube stored as a matrix of four dimensions in the computer 56. For a radiographic system movable only in two dimensions, the legal space table 51 is simply a rectangle having regions of contacting points and non-contacting points that are areas.

The construction of the legal space table 51 substantially simplifies the determination of paths along which the radiographic system 10 can move without collisions. First, the current position of the radiographic system 10 is identified to be a point within the volume of the legal space table 51. Second, the desired path of motion of the radiographic system 10 is broken down into a collection of adjacent points within the legal space table 51. Third, each of these points is examined to ensure that none are in contacting regions 53. Fourth, the legal space table permits a "weighing" of path selections to consider the minimum distance between the system 10 and the patient space for each path selection. The storing of the legal space table as a matrix within the computer 56 provides an extremely rapid means to determine if a particular position of the radiographic system will result in a collision. The coordinates of the position in question are simply looked up in the legal space table 51.

Legal paths, or paths that do not result in a collision of the components of the radiographic system 10, correspond to trajectories within the legal space table 51 made up exclusively of points not within regions 53.

Direction Control

Figure 4:
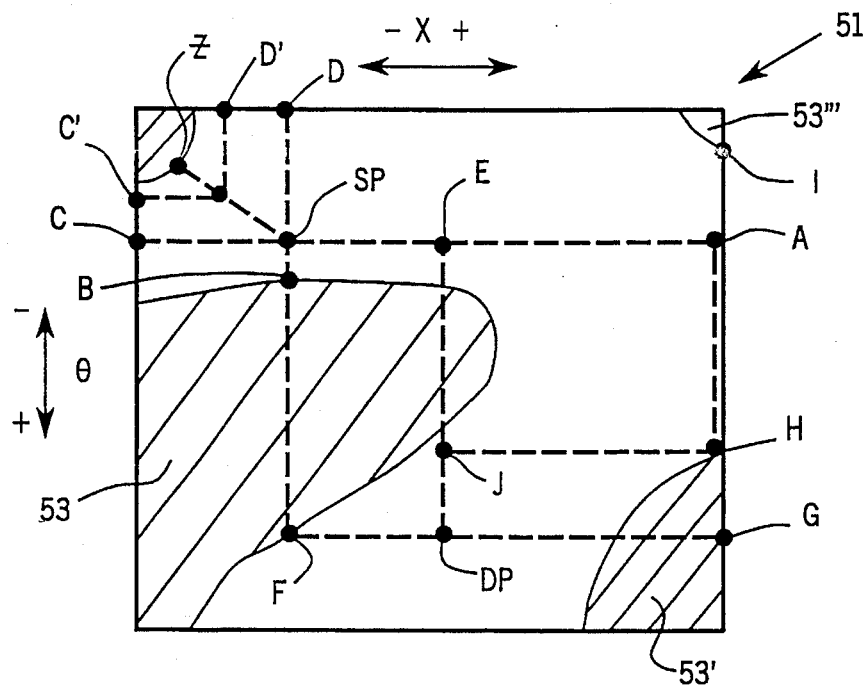
FIG. 4 is a section of the legal space table of FIG. 2 taken along lines 4—4 showing the generation of a legal path when there is no edge path between the source and destination positions.

Referring now to FIGS. 1, 2 and 4, a current position of the radiographic system 10 may be designated as a starting point SP within the legal space table 51. Command signals from the pendant 22 may initiate motion from the starting point in one or more of six directions generally parallel to the axes of the legal space table and in either of two opposite directions.

Upon the operator's depressing one or more of the buttons of the pendant 22, indicating motion of the given axes of the radiographic system 10 in a given direction, the program of the computer 56 invokes an end of travel look-up function ("ELF") which examines each consecutive point of the legal state table 51, in a line along the axes being moved and in the indicated direction, until the first points associated with a contacting state or the edge of the legal state table 51 is found for each such axes.

For example, as shown in FIG. 4, if the command signal from the pendant 22 indicates a positive motion in the θ dimension, the computer program will scan points in the legal space table 51 between point SP and the edge of the legal state table 51 until point B, associated with a contacting region 53, is encountered. This point B is designated as a "soft limit" and continued motion of the axis in the direction indicated by the pendant is allowed by the program only until the soft limit is reached. At that point no further motion in that dimension and direction is allowed.

Simultaneous motion in multiple dimensions x, y or θ is permitted with the use of the pendant 22. With each command signal from the pendant 22, the ELF function is invoked repeatedly to produce a separate soft limit for each of the indicated axes, in the directions indicated by the pendant 22, and based on the then current position of the system 10. So, for example, if the command signal from the pendant 22 indicates simultaneous negative movement in the θ and x axes from point SP to point Z, new soft limits C' and D' will be produced for each point along the path from SP to Z until the limits C' and D' converge at Z. When the system 10 reaches Z, its position will equal the soft limits C' and D' causing motion to cease.

Because the soft limit is a complex function of all three dimensions: x, y and θ, it can be understood that simple mechanical limit switches on the separate axes (which are implicitly functions of only a single axis) cannot provide both collision avoidance and adequate freedom of movement of the radiographic system 10 as is provided by the soft limit system of the present invention.

Point to Point Control

Figure 7:
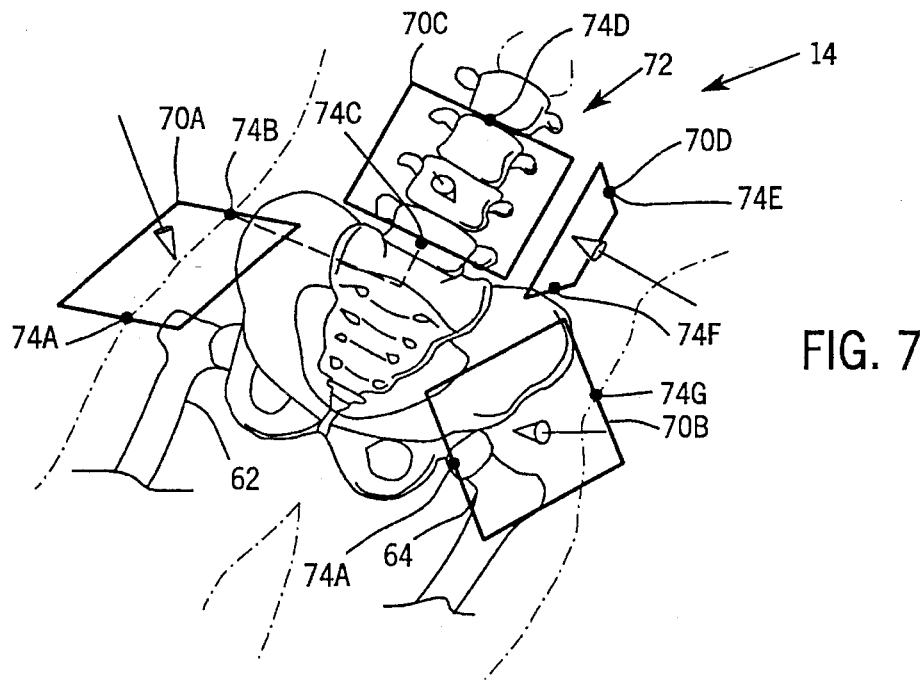
FIG. 7 is a flow chart of a path subroutine called by the program of FIG. 6.
Figure 8:
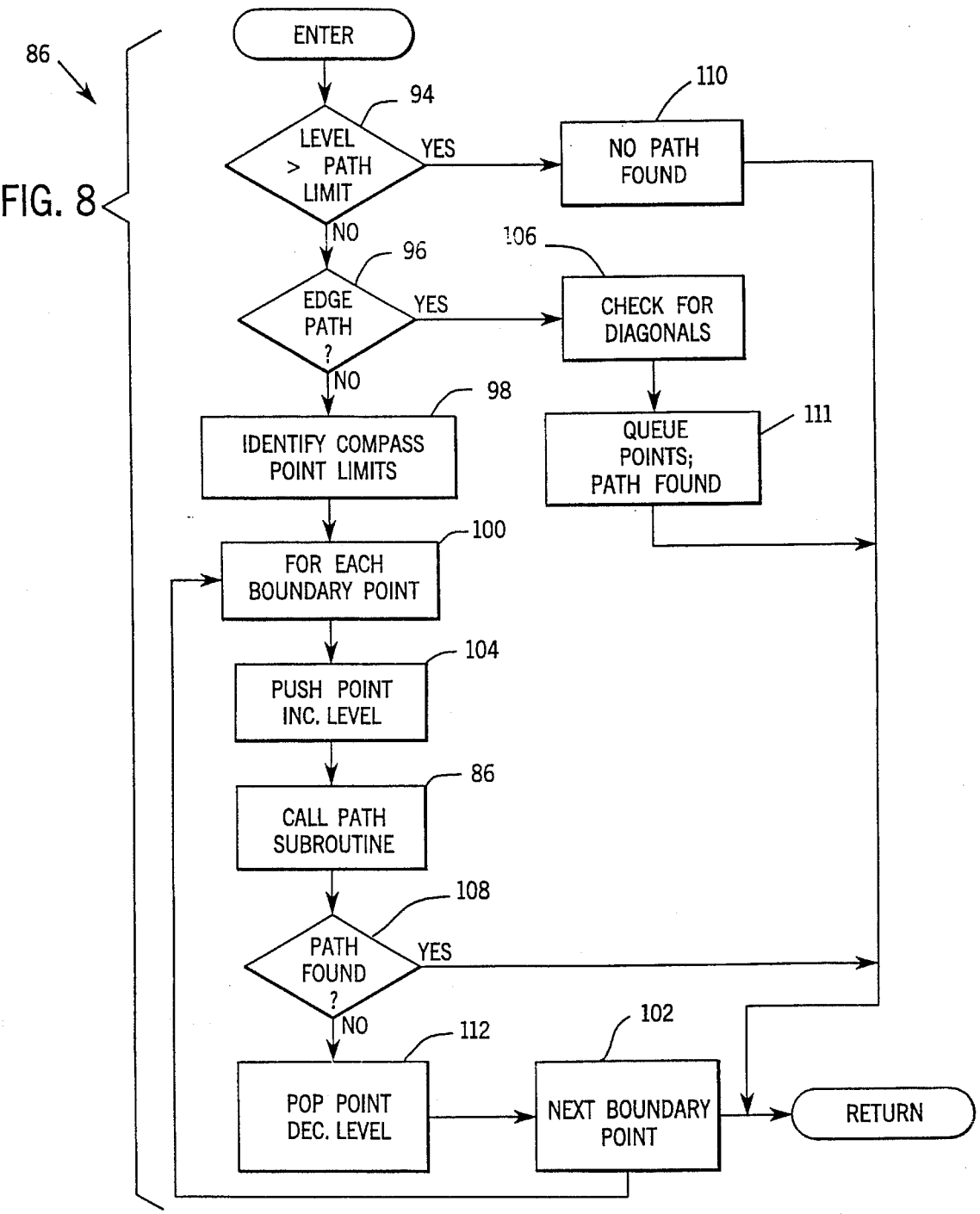
FIG. 8 is perspective view of the lower spine and left and right hip joints showing an automated scanning procedure using the program of FIGS. 6 and 7 to determine legal paths between the individual scans.

Referring now to FIG. 7, in certain circumstances it may be desirable to take standardized sets of images of the patient 14. Each image is defined along a projected image plane 70(*a*)–70(*d*) at different locations and angles about the patient 14. For example, a routine bone density scan might acquire images of the left and right femur 62 and 64 along image planes 70(*a*) and 70(*b*) as well as anterior/posterior and lateral images of the spine 72 at image planes 70(*c*) and 70(*d*).

Ideally an automated procedure would handle the repositioning of the x-ray radiographic system 10 between the acquisition of such images. Thus, for the scanning system shown in FIG. 1, the center of the fan beam might originally be aligned to intersect point 74(*a*) at the center inferior edge of image plane 70(*a*) at an angle somewhat right of the midsagittal plane from an anterior posterior axis. During scanning of the right femur 62, the center of the fan beam 48 would move to point 74(*b*) at the center, superior edge of image plane 70(*a*).

Next, the radiographic system 10 would need to be positioned to align the fan beam axis 49 along the anterior posterior axis at point 74(*c*), the beginning of the AP spinal scan at the center inferior edge of image plane 70(*c*). At the conclusion of the spinal scan, the center of the fan beam would be located at point 74(*d*) superior to point 74(*c*). Angulating the C-arm 40 moves the fan beam to a lateral position to intersect point 70(*e*) at the center superior edge of image plane 70(*d*). At the conclusion of the scan, the center of the fan beam would have moved to point 74(*f*) inferior to point 70(*e*). Finally, at the conclusion of the lateral scan of the lower spine, the radiographic system 10 is positioned to point 74(*g*) to the superior side of the left femur 64 and at a new angle mirroring about the midsagittal plane that angle used to acquire the right femur 62. After the scanning, the radiographic system 10 rests at position 74(*h*) at center inferior edge of image plane 70(*b*) after which it may be returned to the starting point of 74(*a*) in preparation for other patients 14. The location of points 70(*a*) through 70(*h*) relative to each other can be predetermined with respect to an average patient 14 so that image planes 70(*a*)–70(*d*) capture the necessary anatomy of a patient 14 within an expected variation in the population to be scanned. Thus, once position 74(*a*) has been located by an operator with respect to a particular patient 14 on a table 12, the remainder of the scan may proceed automatically with operator supervision.

Figure 6:
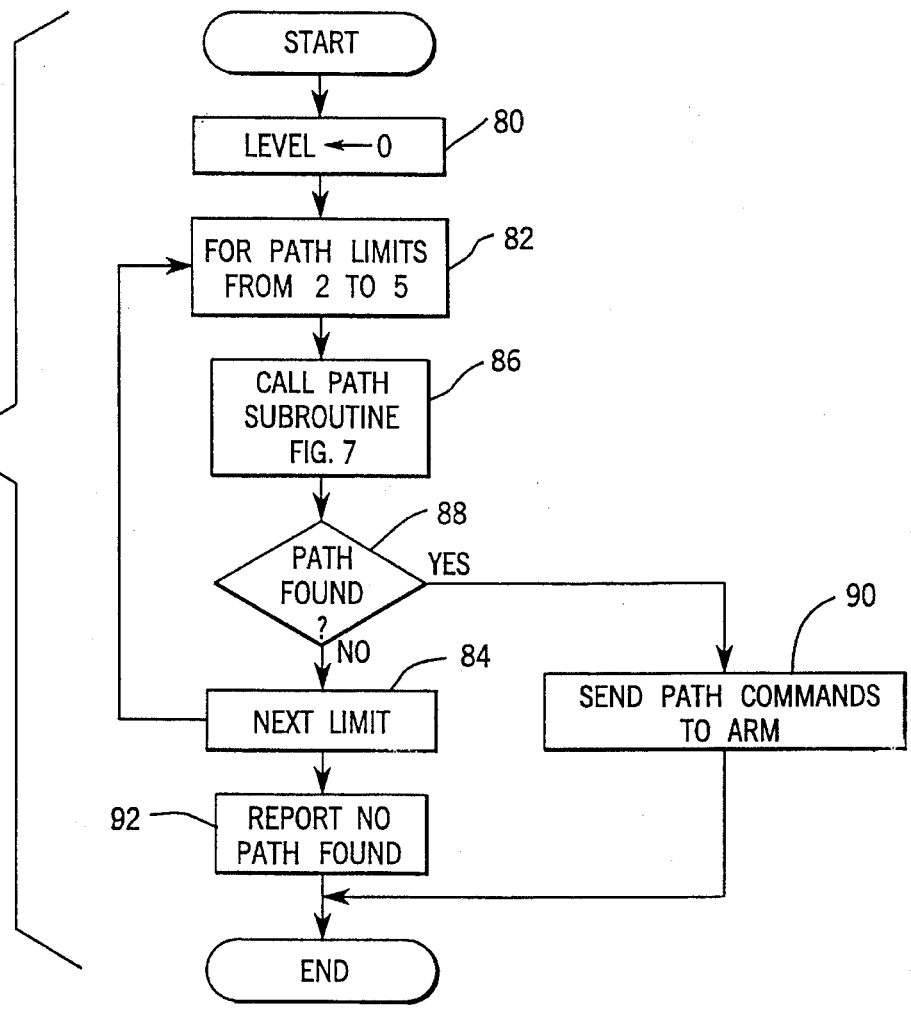
FIG. 6 is a flow chart of the program controlling the computer for the determination of a legal path between two arbitrary points.

For such an automated sequence of scanning between image planes 70, it is necessary to determine paths between the points 74 such that collisions are avoided. Referring now to FIG. 6, a general mapping of a path between a starting point and a destination point can be provided through the use of the legal space table 51 by the program in the computer 58. Generally, the program breaks the path down into a set of simple movements each of which is a legal path, i.e., not crossing points associated with contact regions 53.

Referring now to FIGS. 2, 4 and 6, a path between a starting point, designated SP and a destination point DP is described by a series of legal moves verified by the legal state table 51. Each move is of a single axis at a time, and the number of permissible moves is monitored and limited by a "level" variable that is incremented with each new move. Accordingly, at the beginning of the program, performed by computer 56, the level variable is set to zero at process block 80. Also, a current point CP is identified, initially equal to the starting point SP.

At the next process block 82, which forms a FOR . . . NEXT loop with process block 84, a path limit is set to a number between 2 and 5, starting at a path limit of 2 and for each loop of process blocks 82 and 84, increasing by one until 5 is reached. The path limit sets a practical limit on the number of moves that is acceptable in the path leading from SP to DP. If the path limit of 5 is reached, the loop is exited and a report is generated, at process block 92, that no path (of acceptable length) has been found.

Within the loop formed by process blocks 82 and 84, a "path subroutine", shown in FIG. 7, is called at process block 86. This subroutine, as will be described, endeavors to find a path between SP and DP within the then current path limit. Upon return from the path subroutine, if a path has been found, as determined by process block 88, the program branches to process block 90. Here a path list, giving the endpoints of segments in the legal space table 51 together comprising a legal path, is converted to commands to the motors of the radiographic system 10 and are sent as path commands to the radiographic system 10. Generally, the path commands are in the form of instructions to move a single axis in a single direction until a certain coordinate is reached. Thus they are similar to the commands that may be entered by the pendant 22 as limited by soft limits.

As described above, if no path has been found, as determined by decision block 88, the program proceeds to the NEXT block 84 and the path limit is increased to see if an increase in path limit will yield a path. If the path limit is already at 5, however, after the next limit block 84, the program proceeds to process block 92 and a report is generated on the terminal 58 of the computer 56 that no path has been found and the program ends.

Thus, the path subroutine is invoked successively with increasing path limits being allowed. In this manner, an optimal path will be determined; longer path limits are only tried if no shorter paths have been found by the subroutine of process block 86.

Referring now also to FIG. 7, the path subroutine of process block 86 starts by comparing the level variable originally set in process block to the path limit set by process block 82 in decision block 94. Originally, the level variable will be zero and the path limit will be 2 so at decision block 94, the program will proceed to decision block 96. If, however the level variable has increased beyond the limit of the path limit, the program branches at decision block 94 to return from the subroutine having reset a flag indicating that no path has been found.

Assuming that the path limit has not been exceeded, the program proceeds to decision block 96 where it is determined whether an "edge path" exists between the current point (originally SP) and the destination point DP. At the entry of subroutine 86, the starting point SP is considered the current point.

Referring to FIG. 4, an edge path is a path along the edges of a connection cube 41, having the current point and the destination point as opposite vertices of the cube, that does not cross a region 53. Here the term cube is used generally to be an n-dimensional cube equal in number of dimensions to that of the legal space table 51 and having edges parallel to that of the legal space table 51. The sides of the connection cube 41 need not be of equal length.

Some dimensions of the connection cube 41 may be zero depending on the relative location of the destination point and the current point. For example, assuming that both the current point and the destination point have the same y-axis value, the path problem reduces to two dimensions, and the connection cube 41 connecting the current point CP and the destination point DP will be a rectangle. This is the case with the example of FIG. 4 where the connection cube between points SP and DP is defined by points SP, E, DP, F where point E has a first dimension shared with point CP and a second dimension shared with point DP and point F has a first dimension shared with point DP and a second dimension shared with point CP. In particular, E has the same θ value as CP and the same x value as DP and F has the same θ value as DP and the same x value as CP.

The existence of an edge path is quickly determined by scanning columns or rows of the legal state table 51 along the sides of the connection cube 41 to see if there are any intervening points in a contacting region 53. If a path along one edge of the connection cube 41 connecting CP to DP can be found, then there exists an edge path. Per decision block 96 the program advances to process block 106 and possible diagonal paths are investigated as will be described.

Figure 3:
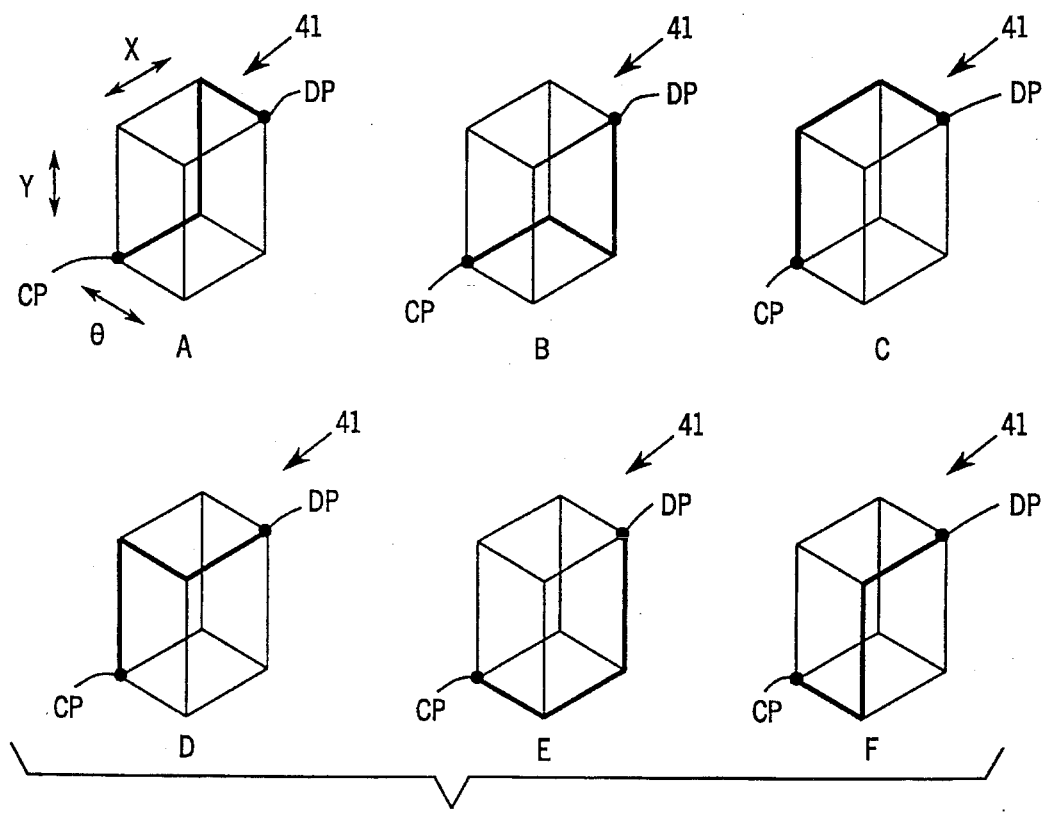
FIG. 3 is a set of six cubes in the legal space table of FIG. 2 showing the six possible edge paths between two opposed vertices representing a source and destination position.

The determination of an edge path is fast because it involves testing relatively few cases. If CP and DP share two coordinates values, there is only a single edge path and the cube devolves to a straight line. When as in FIG. 4, the cube is a rectangle, two edge paths are possible. In the worst case for three dimensions of the legal state table 51, there are six edge paths. As shown in FIG. 3, cube (a) shows an edge path where one traverses first along x then y and then θ. Cube (b) shows traversal first along x then along θ then along y. Cube (c) shows traversal first along y then x and then θ. Cube (d) shows traversal first along y then θ then x. Cube (e) shows traversal first along θ then x then y and finally Cube (f) shows traversal first along θ then y then x. Thus at worst these six paths may be simply tested as described above.

Figure 9:
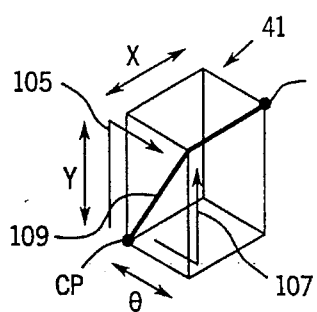
FIG. 9 is a figure similar to that of FIGS. 3(d) and 3(f) showing the method of simplifying the path to a diagonal when multiple edge paths are found.

Referring momentarily to FIGS. 3 and 9, if at process block 96 two edge paths are found that together circumscribe one face of the connection cube 41 (such as paths 105 and 107 shown in FIG. 9 corresponding to the alternative paths of FIGS. 3(d) and 3(f)), then any path within the face may be selected without concern for a possible crossing of a contacting state. Thus a "diagonal" path 109 may be selected providing a shorter distance to traverse.

Similarly, if all edges between the current point CP and the destination point DP are legal edge paths, any path with the volume of the connection cube 41 will be permitted and a "diagonal" path passing between CP and DP directly may be selected. It will be understood from this description that approach may be analogously extended to connection cubes of higher dimension than three.

Note that the relative speed of motion of the axes (θ and x for FIG. 9) is typically not such as to cause the system 10 to follow a true diagonal in the connection cube 41. It is sufficient that the path lie somewhere within the face of the cube when the multiple paths circumscribe a cube face or within the volume of the cube when the multiple paths circumscribe adjacent faces of the connection cube. The term diagonal path should therefore be understood to mean any shorter path whose segments are not aligned with the axes of the connection cube.

In those systems of different architecture where testing the edge paths alone may not reveal whether the entire area or volume within those edge paths is non-contacting space, the complete area or volume of the connection cube may be scanned to determine whether diagonal paths are available, at a corresponding penalty in computation time.

This detection of diagonal paths is conducted at process block 106 and if a diagonal path is found, the endpoints to that path are pushed onto a queue at process block 111. Otherwise the endpoints to the edge path found in decision block 96 are pushed onto the queue at process block 111. In either case, the pushed points provide a map of that path for process block 90 and a flag is set indicating that a path has been found.

As will be understood to those of ordinary skill in the art, a queue is a portion of memory which may accumulate data, preserving the order in which the data is inserted into the queue. Data is removed from the queue in the order in which it is entered in the queue.

If no edge path is found at decision block 96, at process block 98, "compass point limits" are identified with respect to the current point. Referring to FIG. 4, the compass point limits are the limits of movement in each axis direction from the current point. Thus, the compass point limits for SP will be point A in the positive x-direction caused by the end of the legal space table 51, point B in the positive θ direction caused by the interposition of region 53 of contact states, point C in the negative x-direction representing the limit of the legal space table and point D in the negative θ direction also representing the limits of the legal space table 51 along that direction. In the three dimensional case, where point SP and DP do not have the same y-axis values, two more compass point limits will be required indicating the limits in the y directions.

Once the compass point limits have been established as indicated by process block 98, a second FOR . . . NEXT loop formed by process blocks 100 and 102 examine each compass point limit in turn according to a predetermined order starting first with the compass point limit most closely aligned with a line passing directly between the current point and the destination point. This compass point is followed by compass point limits sequentially further from the line passing directly between the current point and the destination point.

In the present example of FIG. 4, the first compass point limit to be examined will be that of point A. At process block 104, point A is pushed onto the queue and the level variable is incremented indicating that the path now has a first segment from point SP to point A.

At this time, the subroutine 86 is called recursively with point A now being the current point and the new value of the level variable as incremented in process block 104 being in force. Thus, decision blocks 94 and 96 are again invoked.

In the present example, the level variable will be 1, still less than the path limit of 2 as tested a process block 94, and an edge path still will not be found per decision block 96. The connection cube 41 in this case would be from point A to point DP along vertices A, G, DP, and E where point G has the same θ value as point DP and the same x value as point A. In this case, point G is within region 53' and segment E, DP crosses region 53. Thus, there is no edge path.

Moving to process block 98, the compass point limits are again determined but for point A, those points being A (because A is already a compass point limit in the x-direction; H being the first point touching region 53 as one moves in the positive θ direction; point C which was also a compass point limit for SP and point I being the soft limit in the negative θ direction from A.

The first compass point limit examined at the beginning of the FOR . . . NEXT loop 100 will be H because the axis of SP and A has been examined already and H is most closely in the direction from A to DP. Point H will be pushed onto the queue and the level variable incremented indicating that the path now has first and second segments SP to A, and A to H.

The path subroutine 86 is again called recursively and decision block 94 passed through because the path limit is 2 and not greater than the path limit of two. At decision block 96, an edge path is examined with a connection cube 41 of vertices H, G, DP, and J where point J has the same θ coordinate as H and the same x-coordinate as DP. An edge path in this case can be constructed of the segments H to J and J to DP. And so at process block 96, the program proceeds to process block 106 where the edge path points J and DP are pushed onto the queue and the path found flag is set.

The program next returns from this level of the path subroutine to arrive back in the previous level of the path subroutine at decision block 108 which checks to see if the path found flag has been set. In this case it has, and so the program branches to a return to the previous level of path subroutine. This process of returning will continue at each level of the nested subroutine until the program returns to the main program of FIG. 6 with the path found flag set. After the test of decision 88, the program will branch to process block 90 where the path commands are sent to the arm.

In certain cases, no path will be found within the path limit of decision block 94. In this case, the path found flag will not be set indicating that no path has been found at process block 108 and the subroutine will return to its previous level. At its previous level, it will encounter decision block 108 querying as to whether a path is found and in cases where no path has been found, the program will branch to process block 112 at which the point previously stored as a path point will be "popped" from the queue (because it was a "dead-end") and the level variable will be decremented indicating the loss of one segment. The program will then branch to the next block 102 and another compass point limit will be inspected unless all compass point limits have been inspected.

If all compass point limits have been inspected (for the given current point) the program will again return, possibly again to a higher level of subroutine, and additional points will be inspected or popped off the queue in a backtracking process until either a suitable path has been found or the program returns to the main program indicating that no path has been found.

Figure 5:
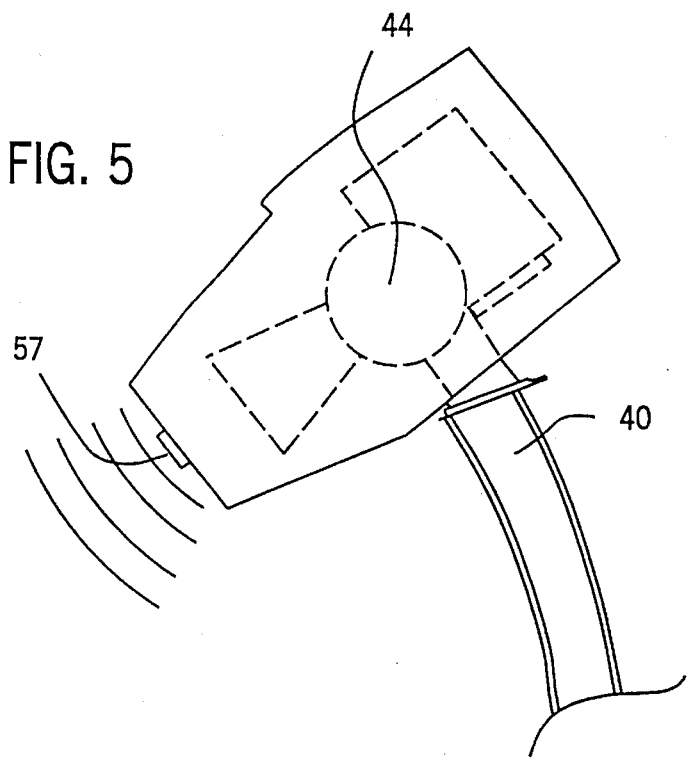
FIG. 5 is a detailed elevational view of the radiation source of FIG. 1 showing placement of an ultrasonic transducer on the x-ray source shroud for augmenting the determination of soft limits through the legal state table of FIG. 2.

Referring now to FIG. 5, the patient 14 cannot always be certain to lie within an envelope incorporated into the legal state table 51 that might otherwise ensure that there can be no contact between the patient 14 and the moving components of the radiographic system 10. For example, the patient 14 may sit up or may have a limb raised from the table 12 or may be of unusual size. For this reason, one or more ultrasonic transducers 57 may be incorporated into various portions of the radiation source 44, arm 40 and detector array 50 so as to detect a close proximity between these surfaces and another surface during control of the radiographic system 10. For example, when the pendant 22 is used to control the radiographic system 10, signals from these ultrasonic transducers 57 received by computer 56 may be used to augment the soft limits obtained from the legal space table 51 or to replace those soft limits if there is a conflict where the ultrasonic transducer 57 indicates that a potential contact is imminent.

The above description has been that of a preferred embodiment of the present invention. It will occur to those that practice the art that many modifications may be made without departing from the spirit and scope of the invention. In order to apprise the public of the various embodiments that may fall within the scope of the invention, the following claims are made.

I claim:

1. A multi-axis radiographic system comprising:
   (1) a radiation source and detector;
   (2) an arm supporting at least one of the radiation source and detector and movable within movement limits to arm positions in at least two dimensions;
   (3) a patient support adapted to position a patient with respect to the arm;
   (4) an operator input device providing command signals to initiate movement of the arm along a movement dimension from a current arm position;
   (5) an electronic computer communicating with the arm so as to determine the arm position and to provide motion signals for moving the arm between arm positions, the electronic computer having a memory storing:
      (a) a legal space table that relates arm positions, within the movement limits of the arm, to one of a contacting and non-contacting state, the contacting state corresponding to one of movement limits and arm positions where there is a high risk of contact between one of the arm, radiation source and radiation detector, and one of the table and patient, and non-contacting states being other arm positions; and
      (b) a program for controlling the electronic computer so as to:
         (i) receive command signals from the operator input device indicating a movement dimension;
         (ii) search the legal space table from the current arm position through arm positions along the movement dimension until a first arm position related to a contact state is found, the first arm position being designated a soft limit; and
         (iii) provide movement signals to the arm to move the arm in the movement dimension only so long as the current arm position is before the soft limit.

2. The multi-axis radiographic system as recited in claim 1 including an ultrasonic range-finder affixed to one of the radiation source, radiation detector and arm providing signals indicating a predetermined proximity between one of the arm, radiation source and radiation detector, and one of the table and patient; and
   wherein the program controls the electronic computer so as to provide movement signals to the arm to move the arm in the movement dimension only so long as the current arm position is before the soft limit and the predetermined proximity has not been reached.

3. A multi-axis radiographic system comprising:
   (1) a radiation source and detector;
   (2) an arm supporting at least one of the radiation source and detector and movable within movement limits to arm positions in at least two dimensions;
   (3) a patient support adapted to positioning a patient with respect to the arm;
   (4) an electronic computer communicating with the arm to provide movement signals for moving the arm between arm positions, the electronic computer having a memory storing:
      (a) a legal space table that relates arm positions, within the movement limits of the arm, to one of a contacting and non-contacting state, the contacting state corresponding to one of movement limits and arm positions where there is a high risk of contact between one of the arm, radiation source and radiation detector, and one of the table and patient, and non-contacting states being other arm positions; and
      (b) a program for controlling the computer so as to:
         (i) determine a destination arm position to which the arm should be moved;
         (ii) determine a legal path through the legal space table from the current arm position to the destination arm position without crossing any arm positions related to the contacting state; and
         (iii) provide movement signals to the arm to move the arm in along the path to the destination arm position.

4. The multi-axis radiographic system as recited in claim 3 wherein the program controls the computer to determine the legal path by:
   a) searching the legal space table from the current arm position to the destination arm position to determine if an edge path exists along edges of an n-dimensional cube in the legal space table having opposed vertices equal to the current arm position and the destination arm dimension, where n is the number of dimensions of the legal space table, the path extending between the current arm position and the destination arm position and not crossing an arm position associated with the contacting state; and
   b) if an edge path exists, using that path as the legal path.

5. The multi-axis radiographic system as recited in claim 3 wherein the program controls the computer to determine the legal path by:
   a) searching the legal space table from the current arm position to the destination arm position to determine if an edge path exists along edges of an n-dimensional cube in the legal space table having opposed vertices equal to the current arm position and the destination arm dimension, where n is the number of dimensions of the legal space table, the path extending between the current arm position and the destination arm position and not crossing an arm position associated with the contacting state; and
   b) if multiple edge paths exist circumscribing at least one face of the n-dimensional cube then using a diagonal path through the n-dimensional cube as the legal path.

6. The multi-axis radiographic system as recited in claim 3 wherein the program controls the computer to determine the legal path by:
   a) searching the legal space table from a first arm position to the destination arm position to determine if an edge path exists along edges of an n-dimensional cube in the legal space table having opposed vertices equal to the first arm position and the destination arm dimension, where n is the number of dimensions of the legal space table, the path extending between the first arm position and the destination arm position and not crossing an arm position associated with the contacting state;
   b) if an edge path cannot be found in step (a), searching the legal space table from the first arm position through arm positions along a movement dimension until an arm position related to a contact state is found, the first arm position being designated a compass point limit;
   (c) repeating steps (a) and (b) using the compass point limit as the first point.

7. The multi-axis radiographic system as recited in claim 5 wherein steps (a) through (c) are repeated for the lesser of a predetermined number of times and the completion of a path.

8. The multi-axis radiographic system of claim 3 wherein steps A through C are repeated for successively greater numbers of times until the completion of a path wherein the shortest such path may be determined.

9. The multi-axis radiographic system as recited in claim 3 including an ultrasonic range-finder affixed to one of the radiation source, radiation detector and arm providing signals indicating a predetermined proximity between one of the arm, radiation source and radiation detector, and one of the table and patient; and wherein the program controls the electronic computer so as to provide movement signals to the arm to move the arm in the movement dimension only so long as the current arm position is before the soft limit and the predetermined proximity has not been reached.

10. The multi-axis radiographic system of claim 3 wherein the program controls the computer to repeat steps (i)–(iii) for a set of different predetermined destination arm positions.

* * * * *